United States Patent [19]

Auel et al.

[11] Patent Number: 4,692,220

[45] Date of Patent: Sep. 8, 1987

[54] ELECTROCHEMICAL DETERMINATION OF FORMALDEHYDE

[75] Inventors: RaeAnn M. Auel, Westminster; Joseph D. Jolson; David A. Stewart, both of Baltimore, all of Md.

[73] Assignee: Mine Safety Appliances Company, Pittsburgh, Pa.

[21] Appl. No.: 822,488

[22] Filed: Jan. 24, 1986

[51] Int. Cl.$^4$ .............................................. G01N 27/46
[52] U.S. Cl. .................................... 204/1 T; 204/412; 204/432
[58] Field of Search ............... 204/1 T, 1 K, 400, 431, 204/432, 412

[56] References Cited

U.S. PATENT DOCUMENTS 3,922,205  11/1975  McLean et al. .................... 204/1 K

OTHER PUBLICATIONS

Bagotsky et al, Electrochemica Acta 9, pp. 869–882 (1964).

Primary Examiner—T. Jung

[57] ABSTRACT

Formaldehyde is determined by electrochemical oxidation of formaldehyde at an iridium electrode while maintaining the electrode at a fixed potential and measuring the current flowing through the electrode.

3 Claims, 3 Drawing Figures

ELECTROCHEMICAL DETERMINATION OF FORMALDEHYDE

FIELD OF THE INVENTION

The invention relates to an electrochemical cell and method for the measurement of formaldehyde in other gases.

BACKGROUND OF THE INVENTION

Formaldehyde is a widely used toxic industrial chemical; the present exposure allowed by the Occupational Safety and Health Administration is 3 ppm TLV for eight hours. Carbon monoxide is also commonly present in industrial environments, so it is necessary in practice for a determination of formaldehyde to be independent of interference from carbon monoxide.

Electrochemical gas sensors and devices are well known in the prior art. See, e.g., U.S. Pat. Nos. 4,184,937; 3,992,267; 3,824,167; and 3,776,832. These sensors and devices are used to detect a variety of noxious gases, including hydrogen sulfide, chlorine, nitric oxide, carbon monoxide and various hydrocarbons.

The electrochemical oxidation of formaldehyde to carbon monoxide has been demonstrated on a platinum electrode [Bagotsky et al., Electrochemica Acta 9, 869 (1964) and Kutschkev, ibid 8, 985 (1963)]. However, continuous exposure of a platinum electrode to formaldehyde results in a reduction in the oxidation current with time. This behavior is typical of electrochemical oxidation of organic compounds on noble metal catalysts, which is characterized by rapid fouling of the electrode. The first electron transfer is fast, usually generating an $H^+$ product and a bound hydrocarbon which does not easily detach from the electrocatalyst. Further, platinum electrodes are also catalytically active to oxidize carbon monoxide, so carbon monoxide interference restricts the use of platinum working electrodes when sensing formaldehyde.

SUMMARY OF THE INVENTION

This invention is based on our discovery that formaldehyde can be selectively oxidized in the presence of CO at an iridium electrode and that the iridium electrode is not rapidly poisoned by exposure to formaldehyde.

The invention is for a method of electrochemically determining formaldehyde in a gas comprising exposing the gas to an iridium electrode in contact with an electrolyte, maintaining the potential of the electrode at a fixed potential of from about 1.1 to 1.5 volts with respect to the reversible hydrogen couple in the electrolyte, whereby formaldehyde is oxidized, and measuring the current flowing through the electrode.

A state of the art electrochemical cell suitable and now preferred for use in practicing the invention includes a working electrode comprising a gas diffusion membrane having a catalytic portion of iridium bonded thereto, a counter electrode, a reference electrode, an electrolyte in contact with the electrodes, and a potentiostat means for maintaining a fixed potential on the working electrode relative to the reference electrode.

DETAILED DESCRIPTION OF THE INVENTION

Figure 1:
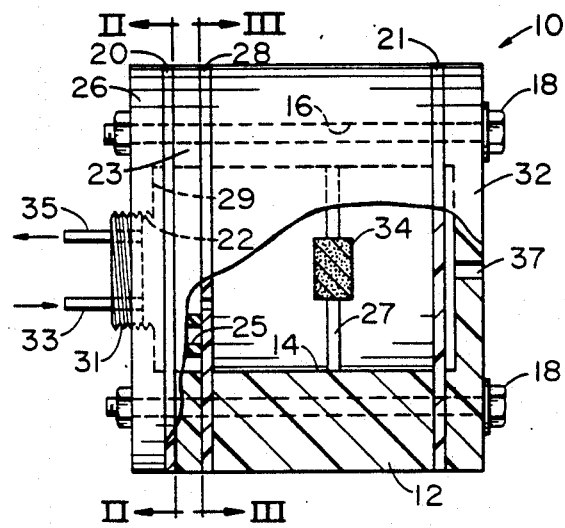
FIG. 1 is an elevation partly cut away of an electrochemical cell used in the practice of the invention.
Figure 2:
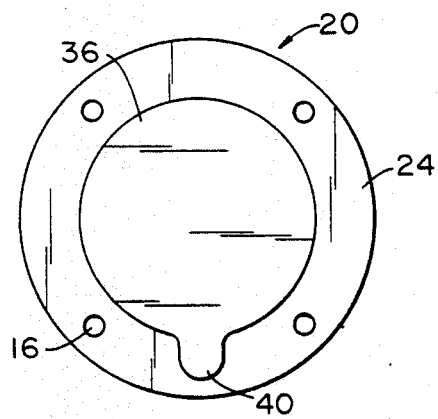
FIG. 2 is an view along line II—II of FIG. 1 showing the working electrode bonded to a membrane.
Figure 3:
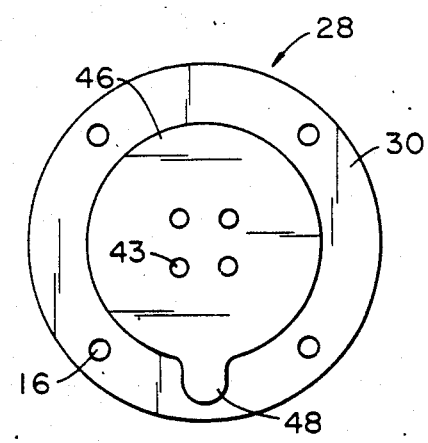
FIG. 3 is an view along line III—III of FIG. 1 showing the counter electrode bonded to a membrane.

Referring to FIG. 1, FIG. 2 and FIG. 3, electrochemical cell 10 comprises a housing 12 having a cavity 14 coextensively positioned therethrough. Housing 12 includes openings 16 to receive mounting bolts 18. Working electrode 20 is sealingly mounted at one end of housing 12 between end plate 26 and electrode spacer 23. The central portion of the electrode spacer has openings 25 permitting the electrolyte to contact the electrodes. Counter electrode 28 is sealingly mounted between spacer holder 23 and housing 12. Membrane 21 is sealingly connected to the other end of housing 12 by end plate 32. End plates 26 and 32 are secured to the respective ends of housing 12 by means of mounting bolts 18 which pass through openings 16 in housing 12 and correlative openings in end plates 26 and 32, spacer 23, electrodes 20 and 28 and membrane 21. Reference electrode 34 is positioned within cavity 14 by suitable positioning means 27, including wire hangers or a friction-fitting reference electrode holder. An electrolyte is contained within the cavity 14 between the electrode 20 and membrane 21.

End plate 26 includes a recess 29 with a threaded opening 22 which exposes a sufficient area of the membrane 24 for diffusion of the environmental or ambient air through the membrane to the working electrode face. A plug 31 having gas inlet 33 and outlet 35 can be screwed into the threaded opening for pumping sampled air at a controlled rate through the chamber formed by recess 29 and electrode 20; air diffuses through the membrane portion 24 of the electrode to the electrolyte/catalyst 36 interface. The use of a flowing sample provides a much higher output for a given formaldehyde concentration than merely exposing the membrane 24 to a quiescent atmosphere. End plate 32 contains a pressure equalizing port 37 open to atmosphere. Gaskets and O-rings (not shown) are used to provide desired sealing of the electrodes, spacer, membrane and end plates to housing 12.

Referring to FIG. 2, working electrode 20 includes a gas diffusion membrane 24 having a catalytic portion 36 of finely divided iridium bonded to it. Catalyst portion 36 also includes tab 49 which is electrically connected to a lead (not shown) for connection to conventional circuitry. Membrane 24 is preferably a Zitex or Goretex porous fluorocarbon membrane. Other membrane materials may be used provided such materials have characteristics similar to Zitex and Goretex, including not becoming wetted by the liquid electrolyte, having a large number of pores (e.g., 50% porous) which in turn have a small pore size, being thin enough to avoid restricting the concentration of the noxious gas being measured and being nonreactive with the atmosphere and electrolyte. Finely divided iridium metal, also called iridium black, is commercially available. It may be necessary to heat the commercial metal in a hydrogen atmosphere, suitably between 400°–600° C., to reduce surface oxides. In accordance with known methods, the electrode 20 is prepared by mixing iridium black with a polytetrafluorethylene (Teflon) dispersion and painting the mixture onto gas diffusion membrane 24. The membrane and catalyst are dried and sintered to provide a good bond.

The counter electrode may be any material, stable in the cell environment, at which oxidation or reduction occurs without limiting the oxidation reaction occurring at the working electrode. With reference to FIG. 3, the counter electrode 28 is an air electrode that includes a gas diffusion membrane 30 and a bonded catalytic portion 46, suitably platinum (platinum black). The catalytic portion of the counter electrode has a tab 48 which is electrically connected to an electrical lead (not shown). Counter electrode 28 also contains holes 43 which allow electrolyte to pass freely to electrode 20. The counter electrode may also be used as the reference electrode for establishing the potential of the working electrode. However, since the potential of the counter electrode will vary with changes in current, it is generally preferred to use a separate reference electrode.

The reference electrode may be any suitable electrode which will operate with the cell and will be stable in the cell environment. Suitable reference electrodes include a normal hydrogen electrode, a saturated calomel electrode, a silver/silver chloride electrode, a glass or pH electrode, a mercury/mercury sulfate electrode, a quinhydrone electrode, a chloranil/graphite electrode, a $Ag/AgSo_4$ electrode, and a platinum/air electrode. Referring to FIG. 1, the reference electrode 34 is a chloranil/graphite electrode, more specifically a pelletized mixture of 50:50 chloranil/graphite, having a current collector electrically connected to a lead (not shown).

The cell electrolyte may be any suitable aqueous, non-aqueous or solid electrolyte which does not react with the electrode at the cell operating potentials and which is capable of supporting ion flow between the first working electrode and the counter electrode, the variety and extent of such electrolytes being within the knowledge of one skilled in the art. The electrolyte and solvent (if any is used) should also exhibit a sufficiently high enough breakdown potential to remain stable and inert at the operating potentials of the cell. Suitable electrolytes include inorganic and organic salts, such as perchloric acid or potassium chloride dissolved in water or in non-aqueous solvents, such as propylene carbonate, dimethylsulfoxide, dimethylforamide, and α-butyrolactone. Suitable solid electrolytes include solid ionic polymers bathed in water, such as perfluorosulfonic acid (Naflon) and perflurocarboxylic acid. The preferred liquid electrolyte is an aqueous electrolyte, with the most preferred electrolyte being an aqueous solution of sulfuric acid.

An important requirement in the method of the present invention is maintaining the working electrode at a fixed potential of from about 1:1 to 1.5 volts with respect to the reversible hydrogen couple in the electrolyte. This may be accomplished by using conventional potentiostats, or potentiostat circuits, that maintain a constant relative potential between the reference and working electrodes.

The working and counter electrodes are connected to circuit means to measure the current flowing through the working electrode, which current is a measure of formaldehyde in the gas exposed to the working electrode. The method of the present invention provides a generally linear response in measuring the formaldehyde, typically providing a 4 to 15 μA output for each ppm of formaldehyde. With conventional state of the art circuitry for measuring current, the detection limit is about 10 ppb of formaldehyde with a sample flow of 1 scfh.

EXAMPLE

Exemplifying the method of this invention, a cell as shown in the drawings was made and tested for response to formaldehyde in the following manner. The working electrode comprised iridium black bonded to a Goretex porous Teflon membrane prepared by mixing 110 mg of iridium black with 150 ml of Dupont TFE dispersion T30 diluted 4 ml to 15 ml deionized water, spreading the mixture on the Goretex membrane and sintering. The effective electrode area was about 7 sq. cm. The counter electrode was platinum black bonded to Zitex, manufactured similarly. The reference electrode was a pellet of 50:50 chloranil/graphite with an embedded wire current collector. A high concentration (12N) sulfuric acid was used as the electrolyte. The working electrode was potentiostated at 700 mV versus the reference electrode (equivalent to 1.48 volts with respect to the reversible hydrogen electrode) and a base current was measured. Air samples containing various amounts of formaldehyde were flowed through the cell at a rate of 300 cc/min. and the current flowing through the working electrode was measured. The current output was about 4 μA/ppm of formaldehyde over a concentration range of about 0 to 26 ppm of formaldehyde. The linearity of the cell was about 95% over 0 to 216 ppm formaldehyde. Even after continuous measurement of a sample of 327 ppm hours of formaldehyde over a period of 11 days, there was no significant change in the response of the cell. Similarly, periodic exposure to formaldehyde containing samples over a four-month period evidenced no significant cell deterioration.

The method is substantially unaffected by carbon monoxide, e.g. in the cell of the example a concentration of about 3175 ppm of carbon dioxide is required to give a current equivalent of 1 ppm of formaldehyde.

Other interferences equivalent to 1 ppm of formaldehyde with the working electrode potentiostated at 700 mv vs. chloranil are:

| | |
|---|---|
| Carbon Dioxide | None |
| Freon | None |
| Nitrous Oxide | None |
| Nitrogen | None |
| Methane | None |
| Hydrogen | 1.5% |
| Nitrogen Dioxide | 305 ppm |
| Acetone | 95 ppm |
| Nitrogen Oxide | 15 ppm |
| Ethylene Oxide | 5 ppm |
| Isopropanol | 4 ppm |

We claim:

1. A method of electrochemically determining formaldehyde in a gas comprising exposing the gas to an iridium electrode in contact with an electrolyte,
   maintaining the electrode at a fixed potential of from about 1.1 to 1.5 volts with respect to the reversible hydrogen couple in the electrolyte, whereby formaldehyde is oxidized, and measuring the current flowing through the electrode.

2. A method according to claim 1 in which the electrode comprises iridium black bonded to a gas permeable membrane.

3. A method according to claim 2 in which the membrane is a fluorocarbon material.

* * * * *